(12) United States Patent
Akiyama et al.

(10) Patent No.: US 7,890,164 B2
(45) Date of Patent: Feb. 15, 2011

(54) IONTOPHORESIS DEVICE

(75) Inventors: Hidero Akiyama, Shibuya-ku (JP);
Mizuo Nakayama, Shibuya-ku (JP);
Takehiko Matsumura, Shibuya-ku (JP);
Akihiko Matsumura, Shibuya-ku (JP)

(73) Assignee: TTI ellebeau, Inc., Tokyo (JP)

( * ) Notice: Subject to any disclaimer, the term of this patent is extended or adjusted under 35 U.S.C. 154(b) by 1189 days.

(21) Appl. No.: 11/522,095

(22) Filed: Sep. 14, 2006

(65) Prior Publication Data

US 2007/0066932 A1    Mar. 22, 2007

Related U.S. Application Data

(60) Provisional application No. 60/729,449, filed on Oct. 21, 2005.

(30) Foreign Application Priority Data

Sep. 15, 2005    (JP)    ............... 2005-268318

(51) Int. Cl.
*A61N 1/30*    (2006.01)
(52) U.S. Cl. ........................... 604/20; 607/1
(58) Field of Classification Search ............. 604/20–21; 607/1, 2, 88
See application file for complete search history.

(56) References Cited

U.S. PATENT DOCUMENTS

| 4,140,121 | A | 2/1979 | Kuhl et al. |
| 4,250,878 | A | 2/1981 | Jacobsen et al. ....... 128/207.21 |
| 4,352,960 | A | 10/1982 | Dormer et al. |
| 4,474,570 | A | 10/1984 | Ariura et al. .................. 604/20 |
| 4,585,652 | A | 4/1986 | Miller et al. .................. 424/83 |
| 4,640,689 | A | 2/1987 | Sibalis ........................ 604/20 |

(Continued)

FOREIGN PATENT DOCUMENTS

CA    2280046    2/1998

(Continued)

OTHER PUBLICATIONS

Cabovska, "Investigations of Separation Mechanisms in Capillary Electrophoresis and High Performance Liquid Chromatography," (2004) Proquest, UMI No. 3120882.

(Continued)

*Primary Examiner*—Nicholas D Lucchesi
*Assistant Examiner*—Theodore J Stigell
(74) *Attorney, Agent, or Firm*—Seed IP Law Group PLLC

(57) ABSTRACT

An shaped iontophoresis device is capable of permeating an active agent (e.g., a drug solution) into an oral cavity, a skin cancer, or the like by iontophoresis in a pinpoint manner. A catheter-type iontophoresis device includes a small working electrode assembly and a small non-working electrode assembly at the tip of a holding portion. A first ion exchange membrane and a fourth ion exchange membrane at the tips of the assemblies are brought into close contact with a target area so that a drug solution is permeated by iontophoresis in a pinpoint manner. The working electrode assembly and the non-working electrode assembly are attached to the tip of a rod-shaped member. The rod-shaped member is detachable from the tip of the holding portion, and is exchangeable integrally with the portion. The iontophoresis device may advantageously take the form of a rod or catheter.

23 Claims, 4 Drawing Sheets

U.S. PATENT DOCUMENTS

| | | | |
|---|---|---|---|
| 4,691,718 A | 9/1987 | Sakuma et al. | 132/84 R |
| 4,702,732 A | 10/1987 | Powers et al. | 604/20 |
| 4,708,716 A | 11/1987 | Sibalis | 604/20 |
| 4,722,726 A | 2/1988 | Sanderson et al. | |
| 4,725,263 A | 2/1988 | McNichols et al. | 604/20 |
| 4,731,049 A | 3/1988 | Parsi | 604/20 |
| 4,744,787 A | 5/1988 | Phipps et al. | |
| 4,747,819 A | 5/1988 | Phipps et al. | |
| 4,752,285 A | 6/1988 | Petelenz et al. | 604/20 |
| 4,764,164 A | 8/1988 | Sasaki | 604/20 |
| 4,786,277 A | 11/1988 | Powers et al. | 604/20 |
| 4,927,408 A | 5/1990 | Haak et al. | |
| 4,931,046 A | 6/1990 | Newman | 604/20 |
| 4,940,456 A | 7/1990 | Sibalis et al. | |
| 4,944,296 A | 7/1990 | Suyama | 128/393 |
| 5,006,108 A | 4/1991 | LaPrade | 604/20 |
| 5,084,006 A | 1/1992 | Lew et al. | |
| 5,084,008 A | 1/1992 | Phipps | |
| 5,115,533 A | 5/1992 | Hukuba | 15/105 |
| 5,135,477 A | 8/1992 | Untereker et al. | |
| 5,135,480 A | 8/1992 | Bannon et al. | 604/20 |
| 5,162,043 A | 11/1992 | Lew et al. | |
| 5,167,616 A | 12/1992 | Haak et al. | 604/20 |
| 5,203,768 A | 4/1993 | Haak et al. | 604/20 |
| 5,206,756 A | 4/1993 | Cheshire | 359/270 |
| 5,224,927 A | 7/1993 | Tapper | 604/20 |
| 5,224,928 A | 7/1993 | Sibalis et al. | 604/20 |
| 5,240,995 A | 8/1993 | Gyory et al. | 525/57 |
| 5,244,557 A | 9/1993 | Defendini et al. | 204/192.29 |
| 5,246,417 A | 9/1993 | Haak et al. | 604/20 |
| 5,284,471 A | 2/1994 | Sage, Jr. | 604/20 |
| 5,290,585 A | 3/1994 | Elton | 427/2 |
| 5,298,017 A | 3/1994 | Theeuwes et al. | 604/20 |
| 5,306,235 A | 4/1994 | Haynes | 604/20 |
| 5,310,404 A | 5/1994 | Gyory et al. | 604/20 |
| 5,312,326 A | 5/1994 | Myers et al. | 604/20 |
| 5,314,502 A | 5/1994 | McNichols et al. | 604/20 |
| 5,320,597 A | 6/1994 | Sage, Jr. et al. | 604/20 |
| 5,320,598 A | 6/1994 | Haak et al. | 604/20 |
| 5,322,502 A | 6/1994 | Theeuwes et al. | 604/20 |
| 5,322,520 A | 6/1994 | Milder | |
| 5,326,341 A | 7/1994 | Lew et al. | |
| 5,338,490 A | 8/1994 | Dietz et al. | 252/500 |
| 5,358,483 A | 10/1994 | Sibalis | 604/20 |
| 5,362,420 A | 11/1994 | Itoh et al. | 252/500 |
| 5,374,241 A | 12/1994 | Lloyd et al. | 604/20 |
| 5,380,271 A | 1/1995 | Gyory | 604/20 |
| 5,380,272 A | 1/1995 | Gross | 604/20 |
| 5,385,543 A | 1/1995 | Haak et al. | 604/20 |
| 5,395,310 A | 3/1995 | Untereker et al. | |
| 5,405,317 A | 4/1995 | Myers et al. | |
| 5,425,703 A | 6/1995 | Feiring | 604/21 |
| 5,445,606 A | 8/1995 | Haak et al. | 604/20 |
| 5,464,387 A | 11/1995 | Haak et al. | 604/20 |
| 5,489,624 A | 2/1996 | Kantner et al. | 524/376 |
| 5,496,266 A | 3/1996 | Haak et al. | |
| 5,503,632 A | 4/1996 | Haak | |
| 5,536,768 A | 7/1996 | Kantner et al. | 524/376 |
| 5,543,098 A | 8/1996 | Myers et al. | |
| 5,551,953 A | 9/1996 | Lattin et al. | 604/20 |
| 5,558,633 A | 9/1996 | Phipps et al. | 604/20 |
| 5,573,503 A | 11/1996 | Untereker et al. | 604/20 |
| 5,573,668 A | 11/1996 | Grosh et al. | 210/490 |
| 5,582,587 A | 12/1996 | Gyory et al. | 604/20 |
| 5,620,580 A | 4/1997 | Okabe et al. | 204/550 |
| 5,623,157 A | 4/1997 | Miyazaki et al. | 257/383 |
| 5,637,084 A | 6/1997 | Kontturi et al. | |
| 5,645,526 A | 7/1997 | Flower | 604/20 |
| 5,647,844 A | 7/1997 | Haak et al. | |
| 5,660,178 A | 8/1997 | Kantner et al. | 128/640 |
| 5,668,170 A | 9/1997 | Gyory | |
| 5,685,837 A | 11/1997 | Horstmann | 604/20 |
| 5,711,761 A | 1/1998 | Untereker et al. | |
| 5,723,130 A | 3/1998 | Hancock et al. | 424/211.1 |
| 5,725,817 A | 3/1998 | Milder | 264/104 |
| 5,730,716 A | 3/1998 | Beck et al. | 604/20 |
| 5,738,647 A | 4/1998 | Bernhard et al. | |
| 5,788,666 A | 8/1998 | Atanasoska | |
| 5,795,321 A | 8/1998 | McArthur et al. | 604/20 |
| 5,800,685 A | 9/1998 | Perrault | 204/291 |
| 5,814,094 A | 9/1998 | Becker et al. | 607/50 |
| 5,817,044 A | 10/1998 | Evers et al. | 604/20 |
| 5,840,056 A | 11/1998 | Atanasoska | |
| 5,871,460 A | 2/1999 | Phipps et al. | |
| 5,919,155 A | 7/1999 | Lattin et al. | 604/20 |
| 5,928,185 A | 7/1999 | Muller et al. | 604/20 |
| 5,941,843 A | 8/1999 | Atanasoska et al. | |
| 5,976,101 A | 11/1999 | Sibalis | 604/20 |
| 5,991,655 A | 11/1999 | Gross et al. | 604/20 |
| 5,995,869 A | 11/1999 | Cormier et al. | 604/20 |
| 6,006,130 A | 12/1999 | Higo et al. | 604/20 |
| 6,032,073 A | 2/2000 | Effenhauser | 604/20 |
| 6,035,234 A | 3/2000 | Riddle et al. | 604/20 |
| 6,047,208 A | 4/2000 | Flower | 604/20 |
| 6,064,908 A | 5/2000 | Muller et al. | |
| 6,086,572 A | 7/2000 | Johnson et al. | 604/503 |
| 6,141,582 A | 10/2000 | Mori et al. | 604/20 |
| 6,167,302 A | 12/2000 | Millot | 604/20 |
| 6,169,920 B1 | 1/2001 | Haak et al. | |
| 6,178,353 B1 | 1/2001 | Griffith et al. | |
| 6,195,582 B1 | 2/2001 | Scott | 604/20 |
| 6,197,324 B1 | 3/2001 | Crittenden | 424/423 |
| 6,201,288 B1 | 3/2001 | Iwasaki et al. | 257/528 |
| 6,223,075 B1 | 4/2001 | Beck et al. | 604/20 |
| 6,228,206 B1 | 5/2001 | Herman et al. | 156/306.9 |
| 6,256,533 B1 | 7/2001 | Yuzhakov et al. | 604/21 |
| 6,289,241 B1 | 9/2001 | Phipps | 604/20 |
| 6,312,612 B1 | 11/2001 | Sherman et al. | 216/2 |
| 6,317,630 B1 | 11/2001 | Gross et al. | 604/20 |
| 6,329,488 B1 | 12/2001 | Terry et al. | 528/28 |
| 6,330,471 B1 | 12/2001 | Higo et al. | 604/20 |
| 6,334,856 B1 | 1/2002 | Allen et al. | 604/191 |
| 6,335,266 B1 | 1/2002 | Kitahara et al. | 438/475 |
| 6,336,049 B1 | 1/2002 | Kinbara et al. | 607/148 |
| 6,350,259 B1 | 2/2002 | Sage, Jr. et al. | |
| 6,377,847 B1 | 4/2002 | Keusch et al. | |
| 6,377,848 B1 | 4/2002 | Garde et al. | |
| 6,379,324 B1 | 4/2002 | Gartstein et al. | 604/22 |
| 6,385,488 B1 | 5/2002 | Flower et al. | |
| 6,394,994 B1 | 5/2002 | Vilambi et al. | |
| 6,402,732 B1 | 6/2002 | Flower et al. | |
| 6,421,561 B1 | 7/2002 | Morris | 604/20 |
| 6,451,240 B1 | 9/2002 | Sherman et al. | 264/504 |
| 6,471,903 B2 | 10/2002 | Sherman et al. | 264/328.1 |
| 6,477,410 B1 | 11/2002 | Henley et al. | 604/20 |
| 6,496,727 B1 | 12/2002 | Bernhard et al. | 604/20 |
| 6,503,231 B1 | 1/2003 | Prausnitz et al. | 604/272 |
| 6,505,069 B2 | 1/2003 | Scott et al. | 604/20 |
| 6,511,463 B1 | 1/2003 | Wood et al. | 604/272 |
| 6,522,919 B1 | 2/2003 | Flower et al. | |
| 6,532,386 B2 | 3/2003 | Sun et al. | 604/20 |
| 6,533,949 B1 | 3/2003 | Yeshurun et al. | 216/11 |
| 6,553,255 B1 | 4/2003 | Miller et al. | |
| 6,560,483 B1 | 5/2003 | Kumar et al. | 604/20 |
| 6,564,092 B1 | 5/2003 | Nakamura et al. | 604/20 |
| 6,565,532 B1 | 5/2003 | Yuzhakov et al. | 604/142 |
| 6,576,712 B2 | 6/2003 | Feldstein et al. | 525/326.9 |
| 6,584,349 B1 | 6/2003 | Sage, Jr. et al. | |
| 6,596,401 B1 | 7/2003 | Terry et al. | 428/447 |
| 6,597,947 B1 | 7/2003 | Inoue et al. | 604/20 |
| 6,603,987 B2 | 8/2003 | Whitson | 600/345 |
| 6,611,707 B1 | 8/2003 | Prausnitz et al. | 604/21 |
| 6,629,968 B1 | 10/2003 | Jain et al. | |
| 6,635,045 B2 | 10/2003 | Keusch et al. | |

| Patent/Pub. No. | Date | Name | Class |
|---|---|---|---|
| 6,654,635 B1 | 11/2003 | Koga et al. | 604/20 |
| 6,663,820 B2 | 12/2003 | Arias et al. | 264/496 |
| 6,678,554 B1 | 1/2004 | Sun et al. | 604/20 |
| 6,678,555 B2 | 1/2004 | Flower et al. | |
| 6,692,456 B1 | 2/2004 | Eppstein et al. | |
| 6,708,050 B2 | 3/2004 | Carim | 600/372 |
| 6,725,090 B1 | 4/2004 | Lattin et al. | 604/20 |
| 6,731,977 B2 | 5/2004 | Beck | |
| 6,735,470 B2 | 5/2004 | Henley et al. | 604/20 |
| 6,743,015 B2 | 6/2004 | Magnani | 433/80 |
| 6,743,432 B1 | 6/2004 | Yanai et al. | 424/400 |
| 6,745,071 B1 | 6/2004 | Anderson et al. | 604/20 |
| 6,767,341 B2 | 7/2004 | Cho | 604/272 |
| 6,775,570 B2 | 8/2004 | Joshi | 604/20 |
| 6,790,372 B2 | 9/2004 | Roy et al. | 216/10 |
| 6,797,276 B1 | 9/2004 | Glenn et al. | 424/278.1 |
| 6,803,420 B2 | 10/2004 | Cleary et al. | 525/205 |
| 6,815,360 B1 | 11/2004 | Canham et al. | 438/706 |
| 6,842,640 B2 | 1/2005 | Riddle et al. | 604/20 |
| 6,855,441 B1 | 2/2005 | Levanon | 429/7 |
| 6,858,018 B1 | 2/2005 | Green et al. | |
| 6,862,473 B2 | 3/2005 | Keusch et al. | |
| 6,881,203 B2 | 4/2005 | Delmore et al. | 604/272 |
| 6,908,453 B2 | 6/2005 | Fleming et al. | 604/173 |
| 6,908,681 B2 | 6/2005 | Terry et al. | 428/447 |
| 6,915,159 B1 | 7/2005 | Kuribayashi et al. | 604/20 |
| 6,918,901 B1 | 7/2005 | Theeuwes et al. | |
| 6,939,311 B2 | 9/2005 | Geiger | 600/573 |
| 6,975,902 B2 | 12/2005 | Phipps et al. | 604/20 |
| 6,994,933 B1 | 2/2006 | Bates | 429/162 |
| 7,018,370 B2 | 3/2006 | Southam et al. | 604/501 |
| 7,033,598 B2 | 4/2006 | Lerner | 424/400 |
| 7,047,069 B2 | 5/2006 | Joshi | 604/20 |
| 7,054,682 B2 | 5/2006 | Young et al. | 604/20 |
| 7,127,285 B2 | 10/2006 | Henley et al. | 604/20 |
| 7,392,080 B2 | 6/2008 | Eppstein et al. | 604/20 |
| 2002/0055704 A1 | 5/2002 | Scott et al. | 604/20 |
| 2002/0099320 A1 | 7/2002 | Beck | 604/20 |
| 2002/0110739 A1 | 8/2002 | McEwen | 429/324 |
| 2002/0123678 A1 | 9/2002 | Lerner et al. | 600/378 |
| 2002/0188241 A1 | 12/2002 | Morris et al. | 604/20 |
| 2003/0018295 A1 | 1/2003 | Henley et al. | 604/20 |
| 2003/0052015 A1 | 3/2003 | Becker et al. | 205/414 |
| 2003/0065305 A1 | 4/2003 | Higuchi et al. | |
| 2003/0135150 A1 | 7/2003 | Kuribayashi et al. | 604/20 |
| 2003/0191426 A1 | 10/2003 | Lerner et al. | 604/20 |
| 2003/0199808 A1* | 10/2003 | Henley et al. | 604/20 |
| 2003/0208152 A1 | 11/2003 | Avrahami et al. | 604/20 |
| 2003/0212397 A1 | 11/2003 | Avrahami et al. | 606/41 |
| 2004/0071765 A1 | 4/2004 | Adachi et al. | 424/449 |
| 2004/0105834 A1 | 6/2004 | Singh et al. | 424/70.13 |
| 2004/0138609 A1 | 7/2004 | Fukuta et al. | |
| 2004/0143210 A1 | 7/2004 | Shevlin | 604/20 |
| 2004/0166147 A1 | 8/2004 | Lundy et al. | 424/449 |
| 2004/0167459 A1 | 8/2004 | Higuchi et al. | |
| 2004/0176737 A1 | 9/2004 | Henley et al. | 604/501 |
| 2004/0176803 A1 | 9/2004 | Whelan et al. | 607/2 |
| 2004/0176805 A1 | 9/2004 | Whelan et al. | 607/2 |
| 2004/0185667 A1 | 9/2004 | Jenson | 438/689 |
| 2004/0225253 A1 | 11/2004 | Shevlin | 604/20 |
| 2004/0247655 A1 | 12/2004 | Asmus et al. | 424/449 |
| 2004/0267169 A1 | 12/2004 | Sun et al. | 601/15 |
| 2004/0267232 A1 | 12/2004 | Sun et al. | 604/500 |
| 2004/0267236 A1 | 12/2004 | Sun et al. | 604/501 |
| 2005/0004506 A1 | 1/2005 | Gyory | 604/20 |
| 2005/0070840 A1 | 3/2005 | Matsumura et al. | |
| 2005/0131336 A1 | 6/2005 | Mori et al. | 604/20 |
| 2005/0143686 A1 | 6/2005 | Shevlin | 604/20 |
| 2005/0148996 A1 | 7/2005 | Sun et al. | 604/501 |
| 2005/0169976 A1 | 8/2005 | Mori et al. | 424/449 |
| 2005/0193554 A1 | 9/2005 | Young et al. | 29/825 |
| 2005/0215944 A1 | 9/2005 | Young et al. | 604/48 |
| 2005/0267440 A1 | 12/2005 | Herman et al. | |
| 2005/0287201 A1 | 12/2005 | Till et al. | 424/450 |
| 2006/0009730 A2 | 1/2006 | Shevlin | 604/20 |
| 2006/0036209 A1 | 2/2006 | Subramony et al. | 604/20 |
| 2006/0043927 A1 | 3/2006 | Beart et al. | |
| 2006/0052739 A1 | 3/2006 | Henley et al. | 604/20 |
| 2006/0095001 A1 | 5/2006 | Matsumura et al. | 604/20 |
| 2006/0135906 A1 | 6/2006 | Matsumura et al. | 604/20 |
| 2006/0247364 A1 | 11/2006 | Murray et al. | 524/495 |
| 2006/0260955 A1 | 11/2006 | Sasaki et al. | 205/759 |
| 2007/0021711 A1 | 1/2007 | Matsumura et al. | 604/20 |
| 2007/0031730 A1 | 2/2007 | Kawakami et al. | 429/218.1 |
| 2007/0048362 A1 | 3/2007 | Nakayama et al. | 424/449 |
| 2007/0060859 A1 | 3/2007 | Kanamura et al. | 604/20 |
| 2007/0060860 A1 | 3/2007 | Nakayama et al. | 604/20 |
| 2007/0060862 A1 | 3/2007 | Sun et al. | 604/20 |
| 2007/0060930 A1 | 3/2007 | Tanioka et al. | 604/20 |
| 2007/0066931 A1 | 3/2007 | Kanamura et al. | 604/20 |
| 2007/0066932 A1 | 3/2007 | Akiyama et al. | 604/20 |
| 2007/0074590 A1 | 4/2007 | Smith | 73/866.1 |
| 2007/0078374 A1 | 4/2007 | Smith | 604/20 |
| 2007/0078375 A1 | 4/2007 | Smith | 604/20 |
| 2007/0078376 A1 | 4/2007 | Smith | |
| 2007/0078445 A1 | 4/2007 | Malloy | 604/890.1 |
| 2007/0083147 A1 | 4/2007 | Smith | 604/20 |
| 2007/0083186 A1 | 4/2007 | Carter et al. | 604/501 |
| 2007/0088332 A1 | 4/2007 | Akiyama et al. | 604/890.1 |
| 2007/0093787 A1 | 4/2007 | Smith | 604/890.1 |
| 2007/0100274 A1 | 5/2007 | Young et al. | 604/20 |
| 2007/0112294 A1 | 5/2007 | Akiyama et al. | 604/20 |
| 2007/0135754 A1 | 6/2007 | Akiyama et al. | 604/20 |
| 2007/0139862 A1 | 6/2007 | Tateishi et al. | 361/502 |
| 2007/0197955 A1 | 8/2007 | Akiyama et al. | 604/20 |
| 2007/0213652 A1 | 9/2007 | Carter | 604/20 |
| 2007/0232983 A1 | 10/2007 | Smith | 604/20 |
| 2008/0033338 A1 | 2/2008 | Smith | 604/20 |
| 2008/0033398 A1 | 2/2008 | Reed et al. | |
| 2008/0114282 A1 | 5/2008 | Carter | |
| 2008/0154178 A1 | 6/2008 | Carter et al. | |

FOREIGN PATENT DOCUMENTS

| | | |
|---|---|---|
| DE | 90 07 277 | 1/1991 |
| EP | 0 097 436 | 1/1984 |
| EP | 0 357 852 A1 | 3/1990 |
| EP | 0 504 715 | 9/1992 |
| EP | 0 824 003 | 2/1998 |
| EP | 0931564 A1 | 7/1999 |
| EP | 1566197 A1 | 8/2005 |
| FR | 2 787 729 A1 | 6/2000 |
| GB | 767343 | 1/1957 |
| GB | 1 219 632 | 1/1971 |
| GB | 2 390 023 A | 12/2003 |
| JP | 63-35266 | 2/1988 |
| JP | 4-297277 | 10/1992 |
| JP | 7-504110 | 5/1995 |
| JP | 8-503875 | 4/1996 |
| JP | 2670794 | 7/1997 |
| JP | 9-248344 | 9/1997 |
| JP | 11-19226 | 1/1999 |
| JP | 11-067236 | 3/1999 |
| JP | 11-076428 | 3/1999 |
| JP | 2901348 | 3/1999 |
| JP | 11-123246 | 5/1999 |
| JP | 11-239621 | 9/1999 |
| JP | 3040517 B2 | 3/2000 |
| JP | 2000-229128 | 8/2000 |
| JP | 2000-229129 | 8/2000 |
| JP | 2000-237326 | 9/2000 |
| JP | 2000-237327 | 9/2000 |
| JP | 2000-237328 | 9/2000 |
| JP | 2000-237329 | 9/2000 |
| JP | 2000-288097 | 10/2000 |
| JP | 2000-288098 | 10/2000 |

| | | |
|---|---|---|
| JP | 2000-316991 | 11/2000 |
| JP | 3119486 | 12/2000 |
| JP | 2001-70459 | 3/2001 |
| JP | 2001-505091 | 4/2001 |
| JP | 2001-120670 | 5/2001 |
| JP | 3290864 | 3/2002 |
| JP | 2002-535100 | 10/2002 |
| JP | 2002-536133 | 10/2002 |
| JP | 2002-541934 | 12/2002 |
| JP | 2003-299743 | 10/2003 |
| JP | 2004-188188 A | 7/2004 |
| JP | 2004-317317 | 10/2004 |
| JP | 2004-357313 | 12/2004 |
| JP | 2005-503194 | 2/2005 |
| JP | 2005-222892 | 8/2005 |
| JP | 2006-149891 | 6/2006 |
| JP | 2006-212194 | 8/2006 |
| JP | 2006-262943 | 10/2006 |
| JP | 2007-075327 | 3/2007 |
| WO | 93/18727 | 9/1993 |
| WO | 94/22528 | 10/1994 |
| WO | 95/35132 | 12/1995 |
| WO | 97/48444 A1 | 12/1997 |
| WO | 98/35722 | 8/1998 |
| WO | 98/56458 | 12/1998 |
| WO | 99/22809 | 5/1999 |
| WO | 99/38565 | 8/1999 |
| WO | 00/44438 | 8/2000 |
| WO | 00/47274 | 8/2000 |
| WO | 00/47274 A1 | 8/2000 |
| WO | 00/62856 | 10/2000 |
| WO | 00/66216 | 11/2000 |
| WO | 01/39830 A2 | 6/2001 |
| WO | 03/037425 | 5/2003 |
| WO | 03/061758 | 7/2003 |
| WO | 2004/028626 A1 | 4/2004 |
| WO | 2005/120631 A1 | 12/2005 |
| WO | 2006/046703 | 5/2006 |
| WO | 2006/062108 | 6/2006 |
| WO | 2008/027218 A2 | 3/2008 |

OTHER PUBLICATIONS

Kalia, Y., et al., "Iontophoretic Drug Delivery," *Advanced Drug Delivery Reviews*, 56:619-658, 2004.
U.S. Appl. No. 11/541,399, filed Sep. 26, 2006, Carter.
U.S. Appl. No. 11/850,600, filed Sep. 5, 2007, Carter.

* cited by examiner

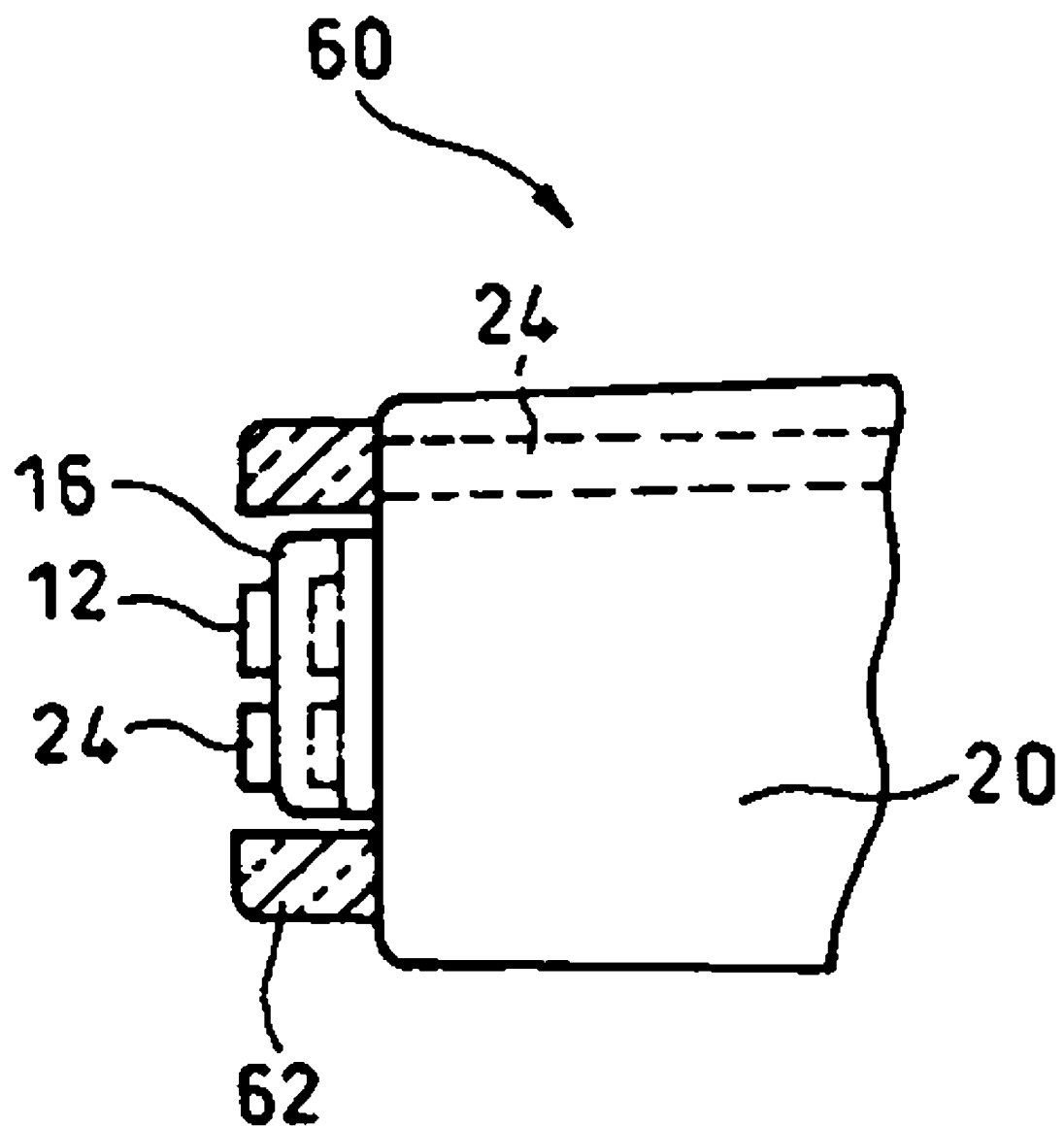

IONTOPHORESIS DEVICE

CROSS-REFERENCE TO RELATED APPLICATION

This application claims the benefit under 35 U.S.C. §119 (e) of U.S. Provisional Patent Application No. 60/729,449, filed Oct. 21, 2005, now pending, which application is incorporated herein by reference in its entirety.

BACKGROUND OF THE INVENTION

1. Field of the Invention

The present disclosure relates to iontophoresis devices for administering an ionic agent, for example a drug ion, to an organism.

2. Description of the Related Art

Iontophoresis devices are intended for permeating an ionized active agent, such as a drug solution, into a skin or a mucous membrane, and have been conventionally used with a skin or mucous membrane having a relatively wide area of at least about 20 mm in diameter.

On the other hand, in the case of, for example, the therapy/treatment in an oral cavity such as the therapy of stomatitis, local anesthesia in an oral cavity, or local anesthesia in odontotherapy, or the therapy of an integument such as melanoma or skin cancer, the direct injection of a drug solution into an affected area as a part (pinpoint) of an organism may increase a therapeutic effect.

In such case, one prefers iontophoresis to injection for permeating a drug solution because the iontophoresis is non-invasive.

Upon photodynamic therapy (PDT), a photosensitized reactive material is administered and irradiated with light, and an anticancer action is expected from the irradiation. However, a patient must be prevented from being irradiated with sunlight because the sensitizer circulates in his or her body. In addition, the sensitizer may circulate in a portion except an affected area to provide a side effect. Therefore, PDT typically requires the administration of a sensitizer only to an affected area.

BRIEF SUMMARY OF THE INVENTION

An iontophoresis device suitably used for permeating a drug solution into a part of an organism that can be observed by a doctor from the outside in, for example, local anesthesia in an oral cavity or the therapy of melanoma is desired.

In one aspect, an embodiment may be summarized as an iontophoresis device including: a working electrode assembly and a non-working electrode assembly each used for administering an ionic drug by iontophoresis; and a DC electric power source connected to the working electrode assembly and the non-working electrode assembly with opposite polarities, characterized by including: a rod-shaped member for supporting the working electrode assembly and the non-working electrode assembly; and a holding portion for detachably supporting the rod-shaped member, the working electrode assembly and the non-working electrode assembly being placed at the tip of the rod-shaped member, and a predetermined amount of spacing being provided between the working electrode assembly and the non-working electrode assembly. The iontophoresis device may, for example, take the form of a rod or a catheter.

In another aspect, an embodiment of the iontophoresis device according to the above may be further summarized as including the ionic drug in the form of a photosensitized reactive material to be activated by absorbing light, and wherein the holding portion has an irradiation optical system for applying light from the vicinity of the tip of the working electrode assembly.

In yet another aspect, an embodiment of the iontophoresis device according to the above may be further summarized as the irradiation optical system including a light source composed of a light-emitting diode or a laser diode for emitting light having a wavelength sensed by the photosensitized reactive material; and an optical fiber to guide light emitted from the light source to the at least proximate rod-shaped member. The iontophoresis device may, for example, take the form of a rod or a catheter.

In still another aspect, an embodiment of the iontophoresis device may be summarized as the holding portion having an electric power source side working electrode terminal and an electric power source side non-working electrode terminal connected to the DC electric power source with opposite polarities through wiring from the DC electric power source, the wiring being housed in the holding portion; the rod-shaped member having on a proximal end of a side thereof detachable from the holding portion a working electrode side contact and a non-working electrode side contact which are connected to or are separated from the electric power source side working electrode terminal and the electric power source side non-working electrode terminal when attached to or detached from the holding portion; and the working electrode side contact and the non-working electrode side contact are connected to a working electrode and a non-working electrode in the working electrode assembly and the non-working electrode assembly, respectively. The iontophoresis device may, for example, take the form of a rod or a catheter.

In yet still another aspect, an embodiment of the iontophoresis device can be summarized as including a controller carried by the holding portion, the controller being placed in an electric power source circuit between the electric power source side working electrode terminal and the electric power source side non-working electrode terminal and the DC electric power source to adjust at least one of a current value during energization and an energization time as administration time. The iontophoresis device may, for example, take the form of a rod or a catheter.

In a further aspect, an embodiment of the iontophoresis device may be summarized as having the working electrode assembly and the non-working electrode assembly placed such that central axes thereof are in parallel with each other.

In yet a further aspect, an embodiment of the iontophoresis device may be summarized as having the working electrode assembly and the non-working electrode assembly placed such that central axes thereof spread out to a tip direction.

In yet still a further aspect, an embodiment of the iontophoresis device may be summarized as having the working electrode assembly and the non-working electrode assembly placed such that central axes thereof intersect each other in a tip direction.

In yet still another further aspect, an embodiment of the iontophoresis device may be summarized as the working electrode assembly includes: the working electrode connected to the DC electric power source having the same polarity as that of a charged ion of the ionic drug; an electrolyte solution holding portion holding an electrolyte solution, the electrolyte solution holding portion being placed on the front surface of the working electrode; a second ion exchange membrane selecting an ion having a polarity opposite to that of the charged ion of the ionic drug, the second ion exchange membrane being placed on the front surface of the electrolyte solution holding portion; a drug solution holding portion holding the ionic drug, the drug solution holding portion being placed on the front surface of the second ion exchange membrane; and a first ion exchange membrane which is the ion exchange membrane selecting an ion having the same polarity as that of the charged ion of the ionic drug, the first ion exchange membrane being placed on the front surface of the drug solution holding portion; and the non-working electrode assembly includes: the non-working electrode connected to the DC electric power source having a polarity opposite to that of the charged ion of the ionic drug; a second electrolyte solution holding portion holding a second electrolyte solution, the second electrolyte solution holding portion being placed on the front surface of the non-working electrode; a third ion exchange membrane selecting an ion having the same polarity as that of the charged ion of the ionic drug, the third ion exchange membrane being placed on the front surface of the second electrolyte solution holding portion; a third electrolyte solution holding portion holding a third electrolyte solution, the third electrolyte solution holding portion being placed on the front surface of the third ion exchange membrane; and a fourth ion exchange membrane which is the ion exchange membrane selecting an ion having a polarity opposite to that of the charged ion of the ionic drug, the fourth ion exchange membrane being placed on the front surface of the third electrolyte solution holding portion.

The working electrode assembly and the non-working electrode assembly in the iontophoresis device are placed at the tip of the rod-shaped member, and the rod-shaped member is detachably supported by the tip of the holding portion. For example, an anticancer agent is permeated by iontophoresis into a pinpoint such as the site of melanoma, whereby efficient therapy can be performed with little side effect. In addition, the drug solution can be exchanged by detaching the working electrode assembly and the non-working electrode assembly together with the rod-shaped member from the support member.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 6 is an enlarged front view showing a main portion of a rod-type iontophoresis device according to Example 2 of the present invention.

FIG. 7 is a left side view of the rod-type iontophoresis device.

DETAILED DESCRIPTION OF THE INVENTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with iontophoresis devices, for example power sources, controllers, regulators, membranes and/or reservoirs have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
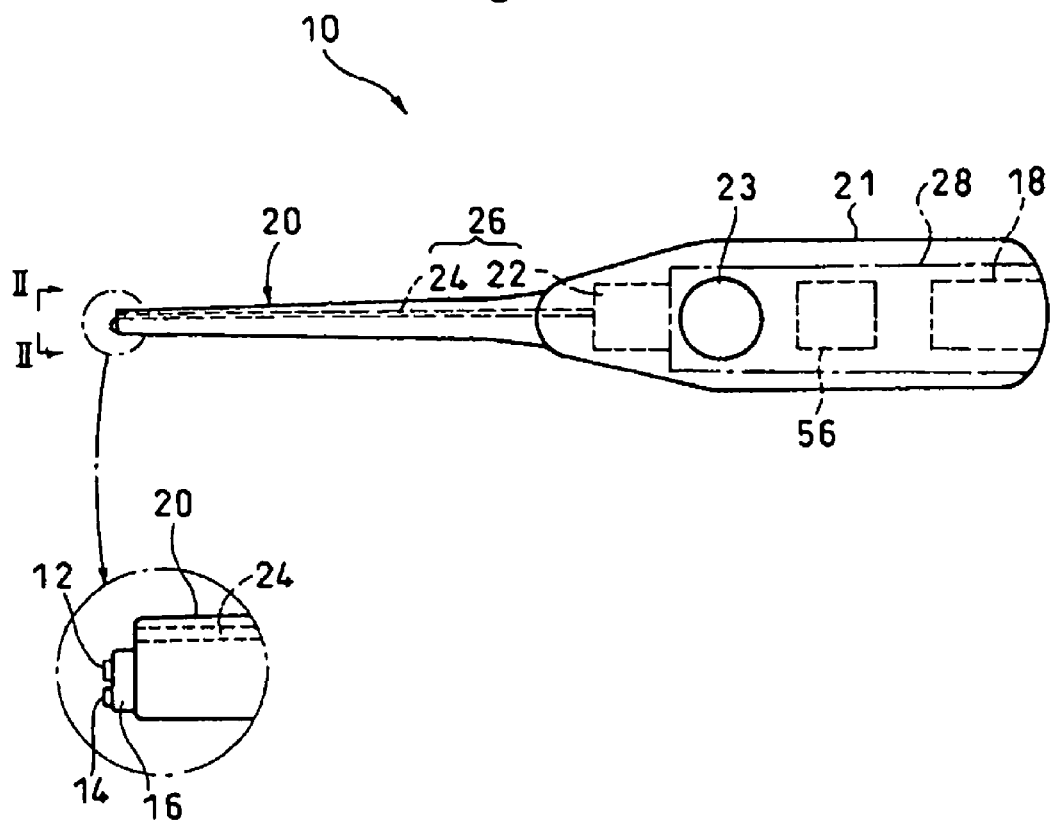
FIG. 1 is a plan view showing an iontophoresis device according to an embodiment of the present invention.
Figure 2:
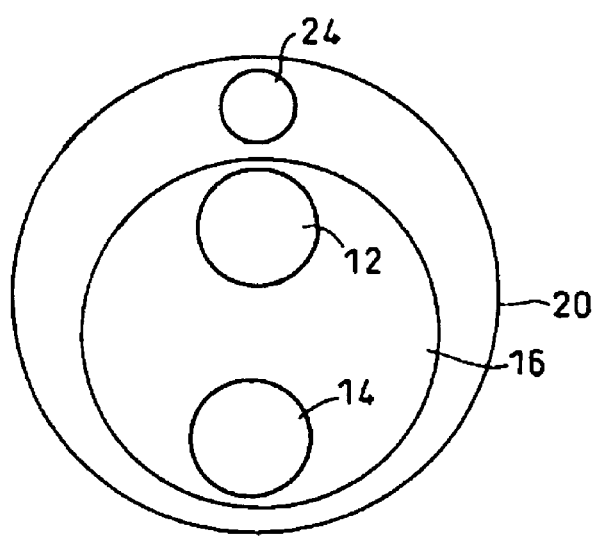
FIG. 2 is an enlarged sectional view taken along the line II-II of FIG. 1.

As shown in FIGS. 1 and 2, an iontophoresis device 10 including a working electrode assembly 12 and a non-working electrode assembly 14 each used for administering an active agent (e.g., an ionic drug), a rod-shaped member 16 for integrally supporting them, and a DC electric power source 18 connected to the working electrode assembly 12 and the non-working electrode assembly 14 with opposite polarities.

The working electrode assembly 12 and the non-working electrode assembly 14 are attached to the tip of the rod-shaped member 16, and the rod-shaped member 16 is detachably supported by the tip of a bar-shaped holding portion 20. As a result, the working electrode assembly 12 and the non-working electrode assembly 14 are exchangeable integrally with the rod-shaped member 16. A proximal end portion of the holding portion 20 opposite to the rod-shaped member 16 serves as a gripping portion 21 having a diameter large enough to be gripped by a human hand.

The holding portion 20 has an irradiation optical system 26 including: an irradiation light source 22 composed of a light-emitting diode (LED) or a laser diode present inside the system; and an optical fiber 24 to guide light emitted from the irradiation light source 22 to a neighborhood of the rod-shaped member 16. As shown in FIG. 2, the optical fiber 24 is placed such that a tip thereof is adjacent to the rod-shaped member 16, and is adapted to emit, from the tip, irradiation light with which an affected area or the like of an organism at a position with which the working electrode assembly 12 can contact is irradiated.

The working electrode assembly 12 and the non-working electrode assembly 14 are connected to different polarities of the DC electric power source 18 through an electric power source circuit 28. The irradiation light source 22 is also connected to the DC electric power source 18 through a switch 23.

An end portion of the rod-shaped member 16 on the side of the holding portion 20 is provided with a working electrode terminal 32 to be connected to the working electrode assembly 12 and a non-working electrode terminal 34 to be connected to the non-working electrode assembly 14.

The working electrode terminal 32 and the non-working electrode terminal 34 are adapted to be electrically connected to an electric power source side working electrode terminal 33 and an electric power source side non-working electrode terminal 35 on the side of the holding portion 20, respectively, when the rod-shaped member 16 is physically attached to the holding portion 20.

The electric power source side working electrode terminal 33 and the electric power source side non-working electrode terminal 35 are further connected to the DC electric power source 30 placed outside through the electric power source circuit 28.

The rod-shaped member 16 may be a cylindrical member having a diameter smaller than that of the tip of the holding portion 20, and may be capable of: being attached by being threaded with a male screw portion 16A into a female screw portion 20A at the tip of the holding portion 20; and being detached by being rotated in the opposite direction. Other attachment or coupling mechanisms are of course possible, for example a bayonet mount mechanism.

Figure 3:
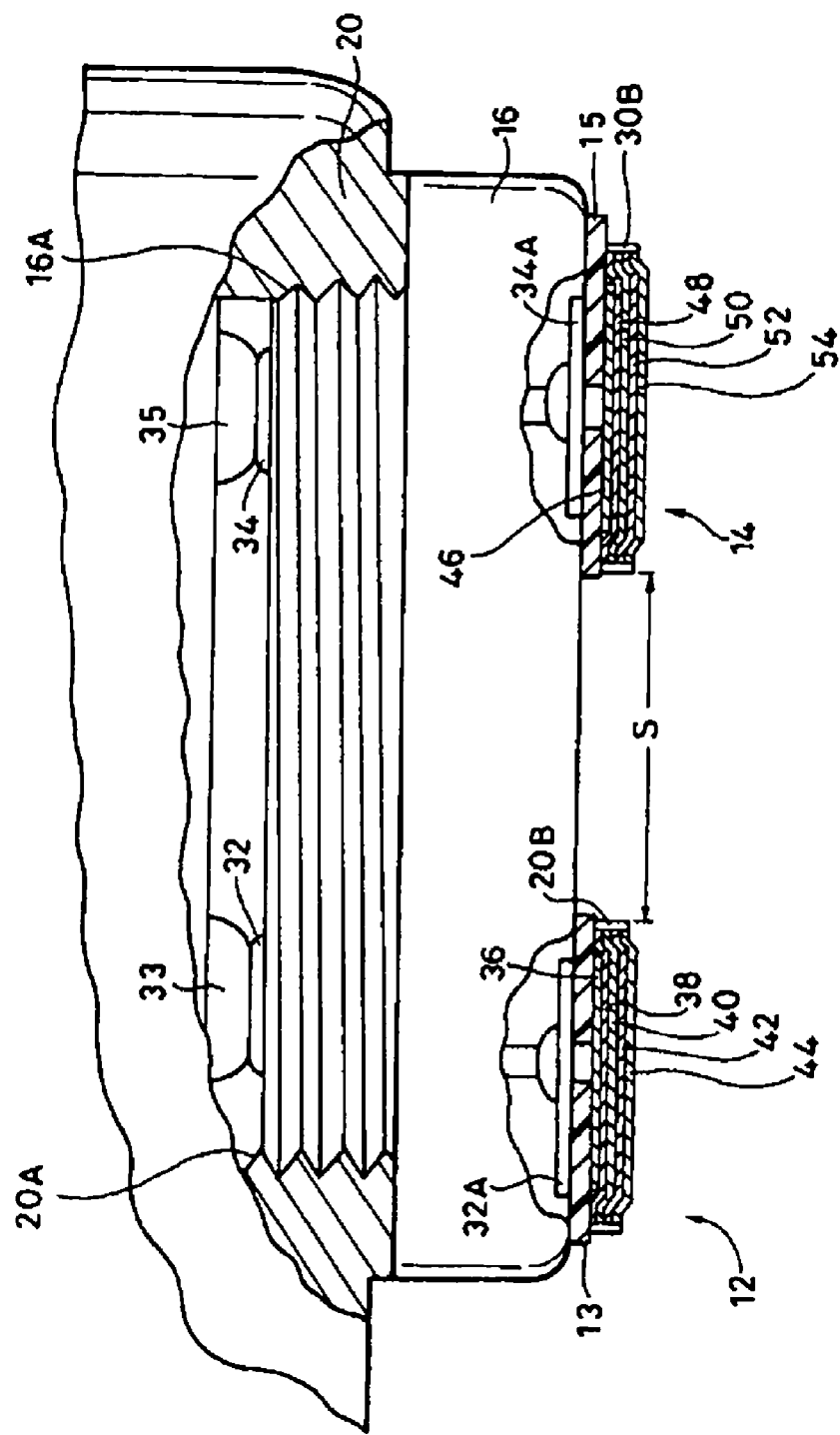
FIG. 3 is an enlarged sectional view showing a main portion of each of a working electrode assembly and a non-working electrode assembly.

FIG. 3 is an enlarged view showing that the working electrode assembly 12 and the non-working electrode assembly 14 are placed such that central axes thereof are in parallel with each other. In addition, the working electrode assembly 12 is constituted by laminating a working electrode 36, an electrolyte solution holding portion 38, a second ion exchange membrane 40, a drug solution holding portion 42, and a first ion exchange membrane 44 in this order from the side of the rod-shaped member 16, and is formed into a disk shape of about 2 to 6 mm in diameter.

The working electrode 36 is desirably constituted by a conductive paint or ink applied to one surface of a base sheet 13 and blended with a nonmetal conductive filler such as a carbon paste. The working electrode 36 can be constituted by a copper plate or a metal thin film, but a metal eluted from the plate or the thin film may transfer to an organism upon administration of a drug. Therefore, the working electrode 36 is preferably nonmetallic.

The electrolyte solution holding portion 38 is constituted by, for example, an electrolytic paint applied to the working electrode 36. The electrolytic paint or ink is a paint or ink containing an electrolyte, and an electrolyte that is oxidized or reduced more easily than the electrolytic reaction of water (oxidation on a positive pole and reduction on a negative pole) is particularly preferably used. Examples of such electrolyte include: medical agents such as ascorbic acid (vitamin C) and sodium ascorbate; and organic acids such as lactic acid, oxalic acid, malic acid, succinic acid, and fumaric acid and/or salts thereof. The use of such electrolyte can suppress the generation of an oxygen gas or a hydrogen gas. In addition, blending multiple kinds of electrolytes serving as a combination of buffer electrolyte solutions when dissolved in a solvent can suppress a change in pH during energization.

The electrolytic paint or ink is blended with a hydrophilic polymer such as polyvinyl alcohol, polyacrylic acid, polyacrylamide, or polyethylene glycol in order to improve the application property and film-forming property of the paint or ink, and is blended with an appropriate amount of solvent such as water, ethanol, or propanol for adjusting the viscosity of the electrolytic paint or ink. The paint or ink may be blended with an appropriate additional component such as a thickener, a thixotropic agent, a defoaming agent, a pigment, a flavor, or a coloring agent.

The second ion exchange membrane 40 is formed by applying a second ion exchange paint or ink to the electrolyte solution holding portion 38.

The second ion exchange paint or ink is a paint or ink containing an ion exchange resin into which an ion exchange group using, as a counter ion, an ion having a conductivity type opposite to that of a drug ion in the drug solution holding portion 42 to be described later is introduced. In the case where a drug whose drug component dissociates to plus drug ions is used in the drug solution holding portion 42, the paint or ink is blended with an anion exchange resin. On the other hand, in the case where a drug whose drug component dissociates to minus drug ions is used, the paint or ink is blended with a cation exchange resin.

The drug solution holding portion 42 is composed of a drug paint or ink applied to the second ion exchange membrane 40. The paint or ink is a paint or ink containing an active agent such as a drug (including a precursor for the drug) whose drug component dissociates to plus or minus ions (drug ions) as a result of, for example, dissolution into a solvent such as water. Examples of a drug whose drug component dissociates to plus ions include lidocaine hydrochloride as an anesthetic drug and morphine hydrochloride as an anesthetic drug. Examples of a drug whose drug component dissociates to minus ions include ascorbic acid as a vitamin agent.

The first ion exchange membrane 44 is formed of a first ion exchange paint or ink applied to the drug solution holding portion 42. The first ion exchange paint or ink is a paint or ink containing an ion exchange resin into which an ion exchange group using, as a counter ion, an ion having the same conductivity type as that of the drug ion in the drug solution holding portion 42 is introduced. In the case where a drug whose drug component dissociates to plus/minus drug ions is used in the drug solution holding portion 42, the paint or ink is blended with an anion/cation exchange resin.

An ion exchange resin obtained by introducing a cation exchange group (an exchange group using a cation as a counter ion) such as a sulfonic group, a carboxylic group, or a phosphoric group into a polymer having a three-dimensional network structure such as a hydrocarbon-based resin (for example, a polystyrene resin or an acrylic resin) or a fluorine-based resin having a perfluorocarbon skeleton can be used as the cation exchange resin without any limitation.

An ion exchange resin obtained by introducing an anion exchange group (an exchange group using an anion as a counter ion) such as a primary amino group, a secondary amino group, a tertiary amino group, a quaternary ammonium group, a pyridyl group, an imidazole group, a quaternary pyridinium group, or a quaternary imidazolium group into a polymer having a three-dimensional network structure similar to that in the case of the cation exchange resin can be used as the anion exchange resin without any limitation.

The non-working electrode assembly 14 is constituted by laminating a non-working electrode 46, a second electrolyte solution holding portion 48, a third ion exchange membrane 50, a third electrolyte solution holding portion 52, and a fourth ion exchange membrane 54 in this order arranged on one surface side of a non-working base sheet 15, and is formed into a disk shape as in the case of the working electrode assembly 12.

The non-working electrode 46 has the same constitution as that of the working electrode 36 in the working electrode assembly 12, and the constitutions and components of the second electrolyte solution holding portion 48 and the third electrolyte solution holding portion 52 are the same as those of the electrolyte solution holding portion 38.

Furthermore, the third ion exchange membrane 50 is formed of an ion exchange paint or ink applied to the second electrolyte solution holding portion 48. The ion exchange paint or ink is the same as the first ion exchange paint or ink of which the first ion exchange membrane 44 is formed, and the third ion exchange membrane 50 functions as an ion exchange membrane similar to the first ion exchange membrane 44.

The fourth ion exchange membrane 54 is formed of the same second ion exchange paint or ink as that described above applied to the third electrolyte solution holding portion 52. The fourth ion exchange membrane 54 functions as an ion exchange membrane similar to the second ion exchange membrane 40.

A working electrode terminal plate 32A is arranged on the other surface of the base sheet 13, and conduction is established between the working electrode terminal plate 32A and the working electrode 36 of the working electrode assembly 12 through a through-hole formed on the base sheet 13, and the working electrode terminal plate 32A is connected to the working electrode terminal 32 through the through-hole.

Similarly, a non-working electrode terminal plate 34A is arranged on the other surface of the non-working base sheet 15, and conduction is established between the non-working electrode terminal plate 34A and the non-working electrode 46 of the non-working electrode assembly 14 through a through-hole formed on the non-working base sheet 15, and the non-working electrode terminal plate 34A is connected to the non-working electrode terminal 34 through the through-hole.

The first ion exchange membrane 44 and the fourth ion exchange membrane 54 at the tips of the working electrode assembly 12 and the non-working electrode assembly 14 are exposed so as to be capable of contacting with the side of an organism, respectively.

The DC electric power source 18 is composed of, for example, an AC/DC converter, and the electric power source circuit 28 between the DC electric power source 18 and the electric power source side working electrode terminal 33 and between the DC electric power source 18 and the electric power source side non-working electrode terminal 35 is provided with a controller 56 for adjusting, at least one of a current value during energization and an energization time as administration time. As a result, each of the current value and the administration time can be adjusted in a certain range.

A predetermined amount of spacing S is provided between the first ion exchange membrane 44 and the fourth ion exchange membrane 54 at each of the tips of the working electrode assembly 12 and the non-working electrode assembly 14 in order to prevent a current from directly flowing between the membranes upon energization. The spacing S has substantially the same size as that of the diameter of each of the first ion exchange membrane 44 and the fourth ion exchange membrane 54.

Figure 4:
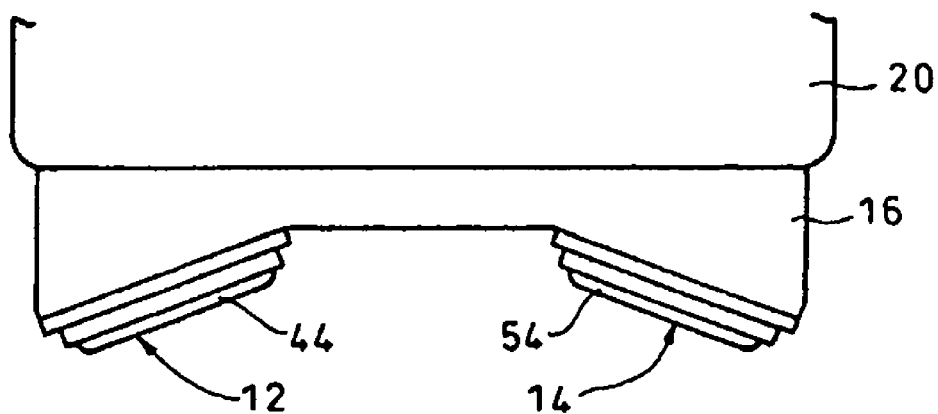
FIG. 4 is a plan view showing another placement example of the working electrode assembly and the non-working electrode assembly.
Figure 5:
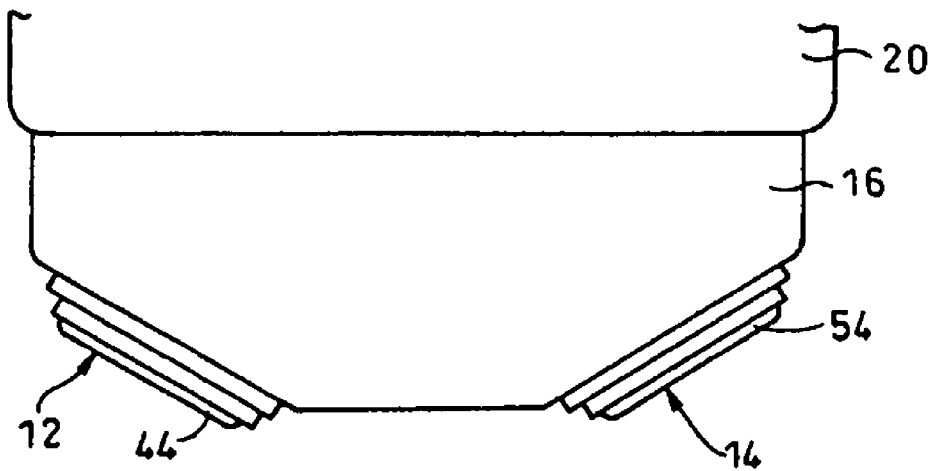
FIG. 5 is a plan view showing still another placement example of the working electrode assembly and the non-working electrode assembly.

In one embodiment, the working electrode assembly 12 and the non-working electrode assembly 14 are attached such that central axes thereof are in parallel with each other. However, the disclosed embodiments are not limited thereto. For example, as shown in FIG. 4, the working electrode assembly 12 and the non-working electrode assembly 14 may be placed such that central axes thereof intersect each other in a tip direction with an angle of, for example, approximately 60° between the axes. Alternatively, as shown in FIG. 5, the working electrode assembly 12 and the non-working electrode assembly 14 may be placed such that central axes thereof spread out to a tip direction.

In such embodiment, the working electrode assembly 12 and the non-working electrode assembly 14 are placed at the tip of the holding portion 20 with the spacing S between them. Therefore, when a drug solution is permeated into an affected area upon therapy or treatment outside a body (such as melanoma or skin cancer) or in a mouth (such as local anesthesia in odontotherapy, the therapy of stomatitis, or local anesthesia in an oral cavity), a doctor grips the gripping portion 21 to bring the first ion exchange membrane 44 at the tip of the working electrode assembly 12 at the tip of the gripping portion 21 into close contact with the affected area and, at the same time, to bring the fourth ion exchange membrane 54 at the tip of the non-working electrode assembly 14 into close contact with a mucous membrane or the like near the affected area for energization. As a result, a target drug solution can be easily permeated into a target site in a pinpoint manner. When the affected area is placed in an oral cavity (that is, in the dark), the affected area in the dark can be illuminated by turning the switch 23 on to irradiate the area with light emitted from the tip of the optical fiber 24 for irradiation of the irradiation optical system 26.

In addition, the working electrode assembly 12 and the non-working electrode assembly 14 can be detached together with the rod-shaped member 16 from the holding portion 20, so a drug solution can be easily exchanged.

The iontophoresis device 10 can be used for, for example, therapy based on photodynamic therapy (PDT) as an anticancer remedy involving: applying a photosensitized reactive material to a cancer cell; and irradiating the material with light to cause the material to absorb the light.

In this case, the following constitution is adopted. That is, the drug solution holding portion 42 in the working electrode assembly 12 holds the photosensitized reactive material, and an affected area can be irradiated with light having a wavelength to be absorbed by the photosensitized reactive material and emitted from the irradiation light source 22 through the optical fiber 24 for irradiation. In the case of PDT, the working electrode assembly 12 is shifted from the affected area after the photosensitized reactive material has been permeated into the affected area by iontophoresis. Then, light to be absorbed by the photosensitized reactive material is applied with the tip of the optical fiber 24 for irradiation as the position of the affected area.

When the affected area has a complicated shape (a two-dimensional convexoconcave figure), a picture is drawn by means of a lightproof insulating paint so that the shape remains on the surface of the first ion exchange membrane 44. Iontophoresis is performed in this state with the iontophoresis device pressed against a skin, whereby the photosensitized reactive material enters only the affected area and, at the same time, the lightproof insulating paint adheres to the periphery of the affected area. That is, the photosensitized reactive material does not enter a normal site and is not irradiated with light. In other words, double or redundant protection can be achieved.

EXAMPLE 1

Next, an iontophoresis device 60 according to Example 2 shown in FIGS. 6 and 7 will be described.

In the iontophoresis device 60, the tip of the holding portion 20 is provided with a ring-like light guide 62 to be coupled to the optical fiber 24 for irradiation, and the working electrode assembly 12 and the non-working electrode assembly 14 are adapted to be capable of sliding back and forth to a cancer together with the rod-like member 16.

The slide structure is identical to a knock structure in a ball-point pen for changing the position of the tip of the pen in two-stages: a projected position and a retracted position. Therefore, detailed description of the slide structure is omitted.

The ring-like light guide 62 is constituted in such a manner that light to be emitted from the tip of the optical fiber 24 for irradiation connected to the light guide is introduced in a ring fashion and outputted from the inner peripheral surface of the guide.

The tip of the light guide 62 at the projected position is adapted to coincide substantially with the tips of the working electrode assembly 12 and the non-working electrode assembly 14.

Accordingly, the rod-shaped member 16 or the like is placed at the projected position upon administration of a drug solution, and the member or the like is placed at the retracted position after the administration of the drug solution. As a result, an affected area to which the drug solution has been administered is separated from the working electrode assembly 12, and the gap between the area and the assembly is irradiated with light from the inner peripheral surface of the light guide 62.

In this example, the holding portion 20 is provided with the optical fiber 24 for irradiation. However, the irradiation optical system 26 including the optical fiber 24 for irradiation may not be needed when the device is not used for PDT or when there is no need to illuminate an affected area.

The various embodiments of the iontophoresis device described above may advantageously take the form of a rod, for example, useful in external application or for use in generally accessible or short lumens or orifices (e.g., mouth, noise, ears, etc.). The various embodiments of the iontophoresis device described above may advantageously take the form of a catheter, for example, useful in generally inaccessible or long lumens or orifices (e.g., arteries, veins, esophagus, intestines, etc.).

DESCRIPTION OF REFERENCE NUMERALS

| | |
|---|---|
| 10, 60 | IONTOPHORESIS DEVICE |
| 12 | WORKING ELECTRODE ASSEMBLY |
| 14 | NON-WORKING ELECTRODE ASSEMBLY |
| 16 | ROD-SHAPED MEMBER |
| 18 | DC ELECTRIC POWER SOURCE |
| 20 | HOLDING PORTION |
| 22 | IRRADIATION LIGHT SOURCE |
| 23 | SWITCH |
| 24 | OPTICAL FIBER FOR IRRADIATION |
| 26 | IRRADIATION OPTICAL SYSTEM |
| 28 | ELECTRIC POWER SOURCE CIRCUIT |
| 32 | WORKING ELECTRODE TERMINAL |
| 33 | ELECTRIC POWER SOURCE SIDE WORKING ELECTRODE TERMINAL |
| 34 | NON-WORKING ELECTRODE TERMINAL |
| 35 | ELECTRIC POWER SOURCE SIDE NON-WORKING ELECTRODE TERMINAL |
| 36 | WORKING ELECTRODE |
| 38 | ELECTROLYTE SOLUTION HOLDING PORTION |
| 40 | SECOND ION EXCHANGE MEMBRANE |
| 42 | DRUG SOLUTION HOLDING PORTION |
| 44 | FIRST ION EXCHANGE MEMBRANE |
| 46 | NON-WORKING ELECTRODE |

-continued

| | |
|---|---|
| 48 | SECOND ELECTROLYTE SOLUTION HOLDING PORTION |
| 50 | THIRD ION EXCHANGE MEMBRANE |
| 52 | THIRD ELECTROLYTE SOLUTION HOLDING PORTION |
| 54 | FOURTH ION EXCHANGE MEMBRANE |
| 56 | CONTROLLER |
| 62 | LIGHT GUIDE |

All of the above U.S. patents, U.S. patent application publications, U.S. patent applications, foreign patents, foreign patent applications and non-patent publications referred to in this specification and/or listed in the Application Data Sheet, including but not limited to U.S. Provisional Application No. 60/729,449, filed on Oct. 21, 2005; and Japanese Patent Application No. 2005-268318, filed on Sep. 15, 2005, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An iontophoresis device, comprising:

a working electrode assembly and a non-working electrode assembly, for use in administering an ionic drug by iontophoresis;

a DC electric power source connected to the working electrode assembly and the non-working electrode assembly with opposite polarities;

a rod-shaped member that supports the working electrode assembly and the non-working electrode assembly;

a holding portion for detachably supporting the rod-shaped member that comprises an electric power source side working electrode terminal and an electric power source side non-working electrode terminal connected to the DC electric power source with opposite polarities through wiring from the DC electric power source, the wiring being housed in the holding portion, the working electrode assembly and the non-working electrode assembly being disposed at a tip of the rod-shaped member, and a predetermined amount of spacing being provided between the working electrode assembly and the non-working electrode assembly, wherein the rod-shaped member comprises on a proximal end of a side thereof detachable from the holding portion a working electrode side contact and a non-working electrode side contact which are electrically connected to, and electrically separated from, the electric power source side working electrode terminal and the electric power source side non-working electrode terminal when the rod-shaped member is respectively physically attached to and detached from the holding portion, and the working electrode side contact and the non-working electrode side contact are connected to a working electrode and a non-working electrode in the working electrode assembly and the non-working electrode assembly, respectively.

2. The iontophoresis device according to claim 1, wherein the working electrode assembly and the non-working electrode assembly are disposed such that central axes thereof are in parallel with each other.

3. The iontophoresis device according to claim 1, wherein the working electrode assembly and the non-working electrode assembly are disposed such that central axes thereof spread out to a tip direction.

4. The iontophoresis device according to claim 1, wherein the working electrode assembly and the non-working electrode assembly are disposed such that central axes thereof intersect each other in a tip direction.

5. An iontophoresis device, comprising:
a working electrode assembly and a non-working electrode assembly, for use in administering an ionic drug by iontophoresis, the ionic drug is formed of a photosensitized reactive material to be activated by absorbing light, and an irradiation optical system for applying light from a vicinity of a tip of the working electrode assembly carried by the holding portion;
a DC electric power source connected to the working electrode assembly and the non-working electrode assembly with opposite polarities;
a rod-shaped member that supports the working electrode assembly and the non-working electrode assembly;
a holding portion for detachably supporting the rod-shaped member;
the working electrode assembly and the non-working electrode assembly being disposed at a tip of the rod-shaped member, and
a predetermined amount of spacing being provided between the working electrode assembly and the non-working electrode assembly.

6. The iontophoresis device according to claims 5, wherein the working electrode assembly and the non-working electrode assembly are disposed such that central axes thereof are in parallel with each other.

7. The iontophoresis device according to claim 5, wherein the working electrode assembly and the non-working electrode assembly are disposed such that central axes thereof spread out to a tip direction.

8. The iontophoresis device according to claims 5, wherein the working electrode assembly and the non-working electrode assembly are disposed such that central axes thereof intersect each other in a tip direction.

9. The iontophoresis device of claim 5 wherein the irradiation optical system comprises:
a light source comprising a light-emitting diode or a laser diode for emitting light having a wavelength to which the photosensitized reactive material reacts; and
an optical fiber to guide light emitted from the light source to at least proximate the rod-shaped member.

10. The iontophoresis device according to claim 9, wherein the working electrode assembly and the non-working electrode assembly are disposed such that central axes thereof are in parallel with each other.

11. The iontophoresis device according to claim 9, wherein the working electrode assembly and the non-working electrode assembly are disposed such that central axes thereof spread out to a tip direction.

12. The iontophoresis device according to claim 9, wherein the working electrode assembly and the non-working electrode assembly are disposed such that central axes thereof intersect each other in a tip direction.

13. The iontophoresis device according to claim 9, wherein:
the holding portion comprises an electric power source side working electrode terminal and an electric power source side non-working electrode terminal connected to the DC electric power source with opposite polarities through wiring from the DC electric power source, the wiring being housed in the holding portion;
the rod-shaped member comprises on a proximal end of a side thereof detachable from the holding portion a working electrode side contact and a non-working electrode side contact which are electrically connected to and electrically separated from the electric power source side working electrode terminal and the electric power source side non-working electrode terminal when the rod-shaped member is respectively physically attached to and detached from the holding portion, and
the working electrode side contact and the non-working electrode side contact are connected to a working electrode and a non-working electrode in the working electrode assembly and the non-working electrode assembly, respectively.

14. The iontophoresis device according to claim 13, wherein the working electrode assembly and the non-working electrode assembly are disposed such that central axes thereof are in parallel with each other.

15. The iontophoresis device according to claim 13, wherein the working electrode assembly and the non-working electrode assembly are disposed such that central axes thereof spread out to a tip direction.

16. The iontophoresis device according to claim 13, wherein the working electrode assembly and the non-working electrode assembly are disposed such that central axes thereof intersect each other in a tip direction.

17. The iontophoresis device of claim 13, further comprising:
a controller carried by the holding portion, the controller being disposed in an electric power source circuit between the electric power source side working electrode terminal and the electric power source side non-working electrode terminal and the DC electric power source operable to adjust at least one of a current value during energization and an energization time.

18. The iontophoresis device according to claim 17 wherein the working electrode assembly and the non-working electrode assembly are disposed such that central axes thereof are in parallel with each other.

19. The iontophoresis device according to claim 17, wherein the working electrode assembly and the non-working electrode assembly are disposed such that central axes thereof spread out to a tip direction.

20. The iontophoresis device according to claim 17, wherein the working electrode assembly and the non-working electrode assembly are disposed such that central axes thereof intersect each other in a tip direction.

21. The iontophoresis device of claim 5 wherein the working and the non-working electrode assemblies are selectively moveable between a projected position and a retracted position.

22. The iontophoresis device of claim 21 wherein the irradiation optical system comprises a ring-like light guide coupled to the optical fiber, the ring-like light guide moveable along with the working and the non-working electrode assemblies.

23. An iontophoresis device, comprising:
a working electrode assembly and a non-working electrode assembly, for use in administering an ionic drug by iontophoresis;
a DC electric power source connected to the working electrode assembly and the non-working electrode assembly with opposite polarities;
a rod-shaped member that supports the working electrode assembly and the non-working electrode assembly;

a holding portion for detachably supporting the rod-shaped member, the working electrode assembly and the non-working electrode assembly being disposed at a tip of the rod-shaped member, and a predetermined amount of spacing being provided between the working electrode assembly and the non-working electrode assembly, and wherein the working electrode assembly comprises:

the working electrode connected to the DC electric power source having the same polarity as that of a charged ion of the ionic drug;

an electrolyte solution holding portion holding an electrolyte solution, the electrolyte solution holding portion being placed on a front surface of the working electrode;

a second ion exchange membrane selecting an ion having a polarity opposite to that of the charged ion of the ionic drug, the second ion exchange membrane being placed on a front surface of the electrolyte solution holding portion;

a drug solution holding portion holding the ionic drug, the drug solution holding portion being placed on a front surface of the second ion exchange membrane; and a first ion exchange membrane selecting an ion having the same polarity as that of the charged ion of the ionic drug, the first ion exchange membrane being placed on a front surface of the drug solution holding portion; and the non-working electrode assembly comprises:

the non-working electrode connected to the DC electric power source having a polarity opposite to that of the charged ion of the ionic drug;

a second electrolyte solution holding portion holding a second electrolyte solution, the second electrolyte solution holding portion being placed on a front surface of the non-working electrode;

a third ion exchange membrane selecting an ion having the same polarity as that of the charged ion of the ionic drug, the third ion exchange membrane being placed on a front surface of the second electrolyte solution holding portion;

a third electrolyte solution holding portion holding a third electrolyte solution, the third electrolyte solution holding portion being placed on a front surface of the third ion exchange membrane; and a fourth ion exchange membrane which is the ion exchange membrane selecting an ion having a polarity opposite to that of the charged ion of the ionic drug, the fourth ion exchange membrane being placed on a front surface of the third electrolyte solution holding portion.

* * * * *